(12) United States Patent
Sato

(10) Patent No.: US 7,911,596 B2
(45) Date of Patent: Mar. 22, 2011

(54) IMAGE PICKUP APPARATUS

(75) Inventor: Hideo Sato, Tokyo (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 12/607,752

(22) Filed: Oct. 28, 2009

(65) Prior Publication Data

US 2010/0045973 A1 Feb. 25, 2010

Related U.S. Application Data

(63) Continuation of application No. 11/380,131, filed on Apr. 25, 2006, now Pat. No. 7,692,774.

(30) Foreign Application Priority Data

Apr. 28, 2005 (JP) .................................. 2005-132883

(51) Int. Cl.
   *G06K 9/74* (2006.01)
(52) U.S. Cl. ........................... 356/71; 382/124; 382/126
(58) Field of Classification Search ..................... 356/71; 382/124, 126
   See application file for complete search history.

(56) References Cited

U.S. PATENT DOCUMENTS

| 5,177,802 | A | * | 1/1993 | Fujimoto et al. | ............... 382/124 |
| 5,448,659 | A | * | 9/1995 | Tsutsui et al. | .................. 385/14 |
| 6,956,608 | B1 | * | 10/2005 | Shapiro et al. | ................ 348/335 |
| 2005/0154318 | A1 | | 7/2005 | Sato | |
| 2007/0019845 | A1 | * | 1/2007 | Kato | ............................ 382/126 |

FOREIGN PATENT DOCUMENTS

| JP | 06-282637 | 10/1994 |
| JP | 2001-052151 | 2/2001 |
| JP | 2002-312771 | 10/2002 |
| JP | 2004-310577 | 11/2004 |
| JP | 03-256185 | 11/2005 |
| JP | 2000-030034 | 10/2010 |

OTHER PUBLICATIONS

Japanese Office Action for corresponding JP2005-132883 issued on Oct. 14, 2010.

* cited by examiner

*Primary Examiner* — Roy Punnoose
(74) *Attorney, Agent, or Firm* — K&L Gates LLP

(57) ABSTRACT

The present invention provides an image pickup apparatus with a thin-shaped body. The image pickup apparatus includes: emitter means 8 for emitting an imaging light; light transmission means for leading the imaging light that comes from one face directly to another face, and leading the imaging light that comes from a certain position of the another face to a different position of the one face; and image pickup means for picking up an image equivalent to the imaging light from the light transmission means. Therefore, the emitter means can be placed substantially on the same plane as the image pickup means under the one face M1 of the light transmission means. Thus, the body of the image pickup apparatus can be thinner.

20 Claims, 12 Drawing Sheets

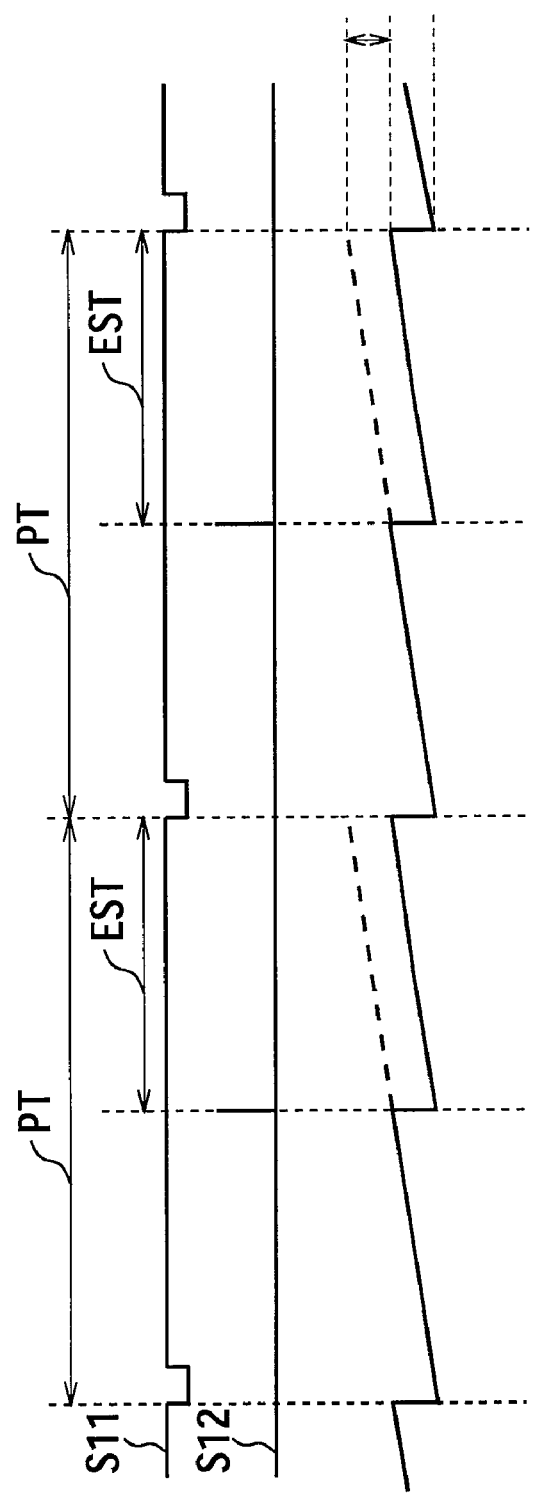

IMAGE PICKUP APPARATUS

CROSS REFERENCES TO RELATED APPLICATIONS

The present application is a continuation of U.S. patent application Ser. No. 11/380,131 filed on Apr. 25, 2006 which claims priority to Japanese Patent Application JP2005-132883 filed in the Japanese Patent Office on Apr. 28, 2005, the entire contents of which is being incorporated herein by reference.

BACKGROUND

The preset invention relates to an image pickup apparatus, and is preferably utilized to take an image of blood vessels inside a living body for authentication, for example.

Biometric authentication uses blood vessels as a target of authentication. Since the main absorbers of Near-InfraRed (NIR) light in the blood vessels are deoxy-hemoglobin (venous blood) and oxy-hemoglobin (arterial blood), an image pickup device, which is for example disclosed in Jpn. Pat. Appln. Laid-open Publication No. 2004-135609 (FIGS. 1, 3 and 10), can take an image of the blood vessels by utilizing the characteristics of NIR light.

This kind of image pickup device has NIR light sources on the surface of its housing. The NIR light sources emit NIR light to a finger placed on an image pickup aperture. In this case, the NIR light has higher intensity than ordinary light in the atmosphere (the ordinary light includes visible light around the finger). The NIR light goes into the finger and then comes out from the pad of the finger. This NIR light is led to an imaging plane of a Charge Coupled Device (CCD) via an optical lens and an ultraviolet filter to project the blood vessels.

The image pickup device then utilizes photoelectric transducers on the imaging plane of the CCD to perform photoelectric conversion. This increases/decreases electric charges in the CCD per unit time to improve the imaging sensitivity of the CCD to the NIR light.

This image pickup device does not have any physical shields to shut out ordinary light, because it can electrically reduce noise generated from ordinary light. Therefore, the image pickup device can be small.

SUMMARY

By the way, in the above-noted image pickup device, the NIR light sources are disposed on the surface of the housing, while the CCD is disposed inside the housing. And the NIR light sources are placed right above the CCD such that they are close to an optical axis. This makes the image pickup device bulky.

The present invention has been made in view of the above points and is intended to provide an image pickup apparatus with a thin-shaped body.

In an embodiment of the present invention, an image pickup apparatus includes: emitter means for emitting an imaging light; light transmission means for leading the imaging light that comes from one face directly to another face, and leading the imaging light that comes from a certain position of the another face to a different position of the one face; and image pickup means for picking up an image equivalent to the imaging light from the light transmission means.

Therefore, the emitter means can be placed substantially on the same plane as the image pickup means under the one face of the light transmission means.

In this manner, the image pickup apparatus according to an embodiment of the present invention includes: emitter means for emitting an imaging light; light transmission means for leading the imaging light that comes from one face directly to another face, and leading the imaging light that comes from a certain position of the another face to a different position of the one face; and image pickup means for picking up an image equivalent to the imaging light from the light transmission means. Therefore, the emitter means can be placed substantially on the same plane as the image pickup means under the one face of the light transmission means. Thus, the body of the image pickup apparatus can be thinner.

The nature, principle and utility of the present invention will become more apparent from the following detailed description when read in conjunction with the accompanying drawings in which like parts are designated by like reference numerals or characters.

Additional features and advantages are described herein, and will be apparent from, the following Detailed Description and the figures.

BRIEF DESCRIPTION OF THE FIGURES

FIGS. 6A to 6C are timing charts illustrating a drive control method of CCD imaging elements.

DETAILED DESCRIPTION

An embodiment of the present invention will be described in detail with reference to the accompanying drawings.

(1) First Embodiment

Figure 1:
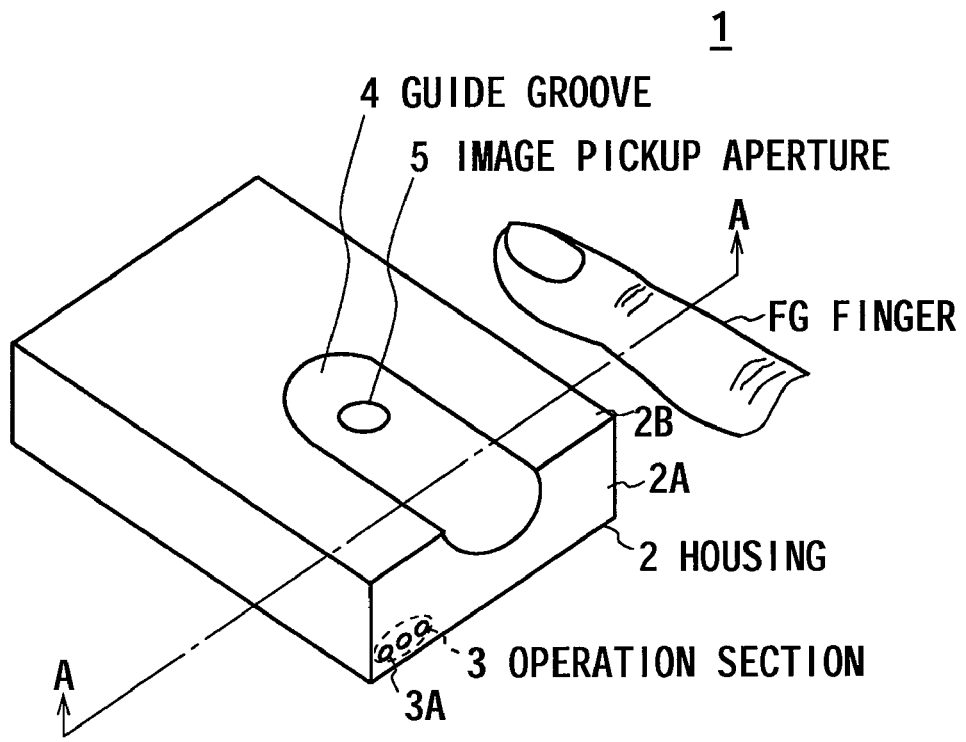
FIG. 1 is a schematic diagram showing the external structure of an authentication device according to a first embodiment of the present invention.
Figure 2:
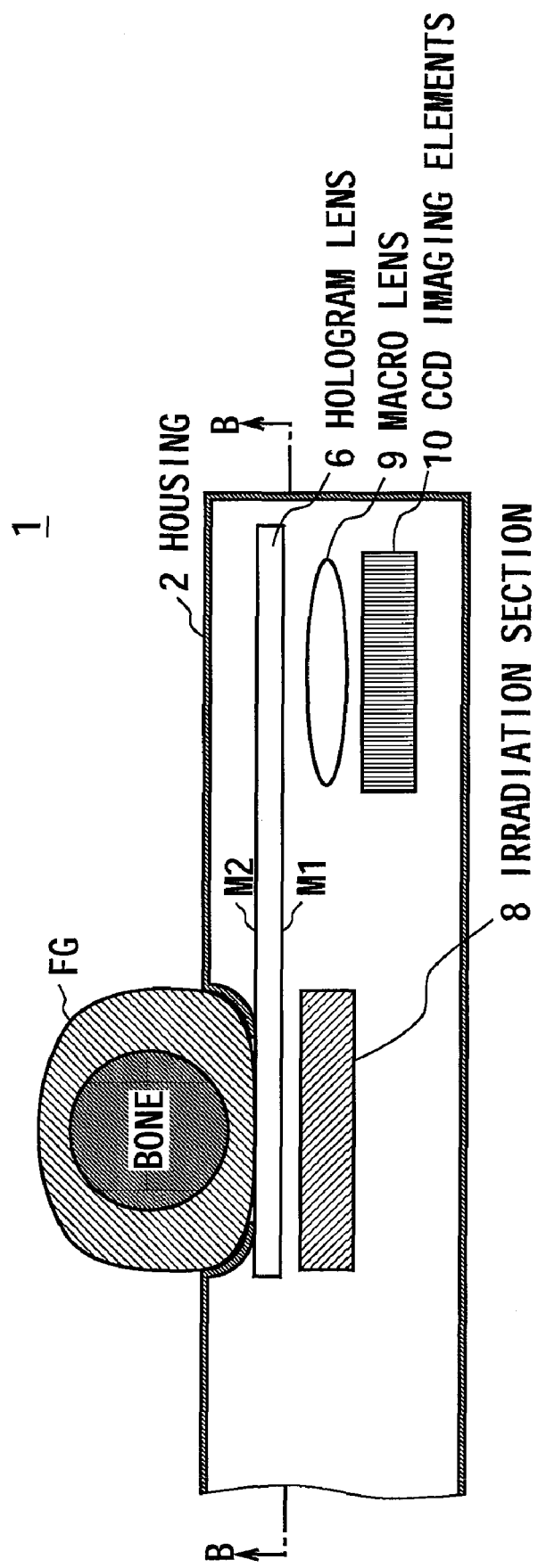
FIG. 2 is a schematic diagram showing the internal structure of the authentication device.

(1-1) Overall Configuration of Authentication Device According to First Embodiment In FIGS. 1 and 2 (FIG. 2 is a cross-section view of a housing 2 taken along the line A-A' in FIG. 1), the reference numeral 1 represents an authentication device according to a first embodiment of the present invention. The authentication device 1 has the housing 2, which is generally in the shape of a rectangular parallelepiped. On a side face 2A, which is the front side of the housing 2, an operation section 3 is disposed. The operation section 3 includes an image-pickup start button 3A. On an upper surface 2B of the housing 2, a guide groove 4 with a certain width is formed from one side of the housing 2 (i.e. the side face 2A) to a central part of the housing 2 to fit the shape of a finger.

An image pickup aperture 5 is formed through a bottom face of the guide groove 4 near a foremost part of the guide groove 4. A hologram lens 6 is disposed inside the housing 2 such that the hologram lens 6 covers the image pickup aperture 5 from the inside. This prevents foreign matter from getting into the inside of the housing 2, while a finger FG can be placed on the surface of the hologram lens 6 which is located immediately beneath the image pickup aperture 5.

The hologram lens 6, which is in the shape of a flat plate, is substantially parallel to the upper surface 2B of the housing 2. One side of hologram lens 6, which is located under the image pickup aperture 5, leads light from a back face (one face) M1 directly to a surface (another face) M2. In addition, inside the hologram lens 6, a reflection path is formed from the surface M2 around the one side of hologram lens 6 to the back face M1 around the other side of hologram lens 6 to lead light from the one side to the other side.

Figure 3:
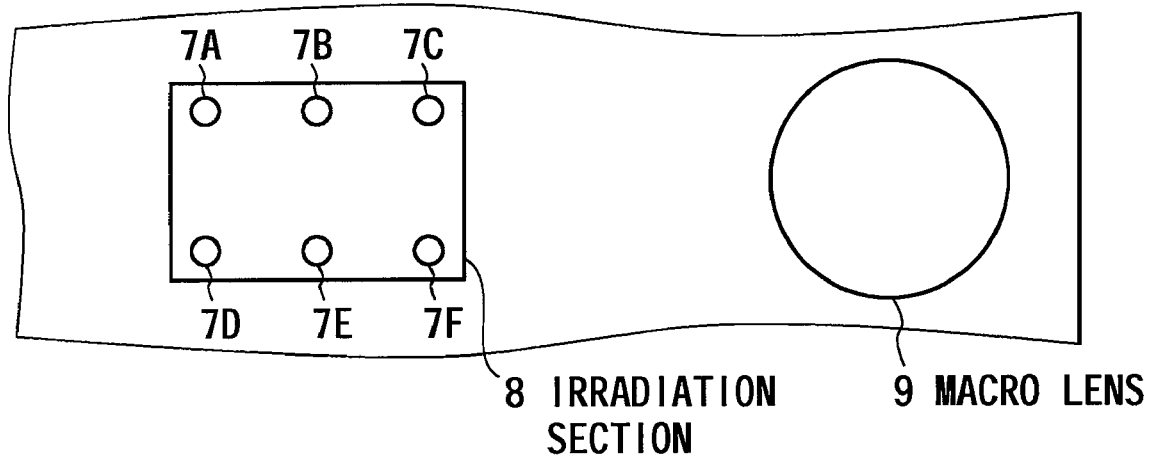
FIG. 3 is a schematic diagram showing the configuration of NIR light sources.

Under the back face M1, an irradiation section 8 is disposed right below the one side of hologram lens 6. As shown in FIG. 3 (FIG. 3 is a cross-section view of the housing 2 taken along the line B-B' in FIG. 2), the irradiation section 8 includes a plurality of Near-InfraRed (NIR) light sources 7 (7A through 7F). The NIR light sources 7, which emit NIR light to take a picture of blood vessels, are placed in a certain configuration. Under the other side of hologram lens 6, a macro lens 9 and CCD imaging elements 10 are disposed such that light that comes out from the other side of hologram lens 6 goes to an imaging plane of the CCD imaging elements 10.

Figure 4:
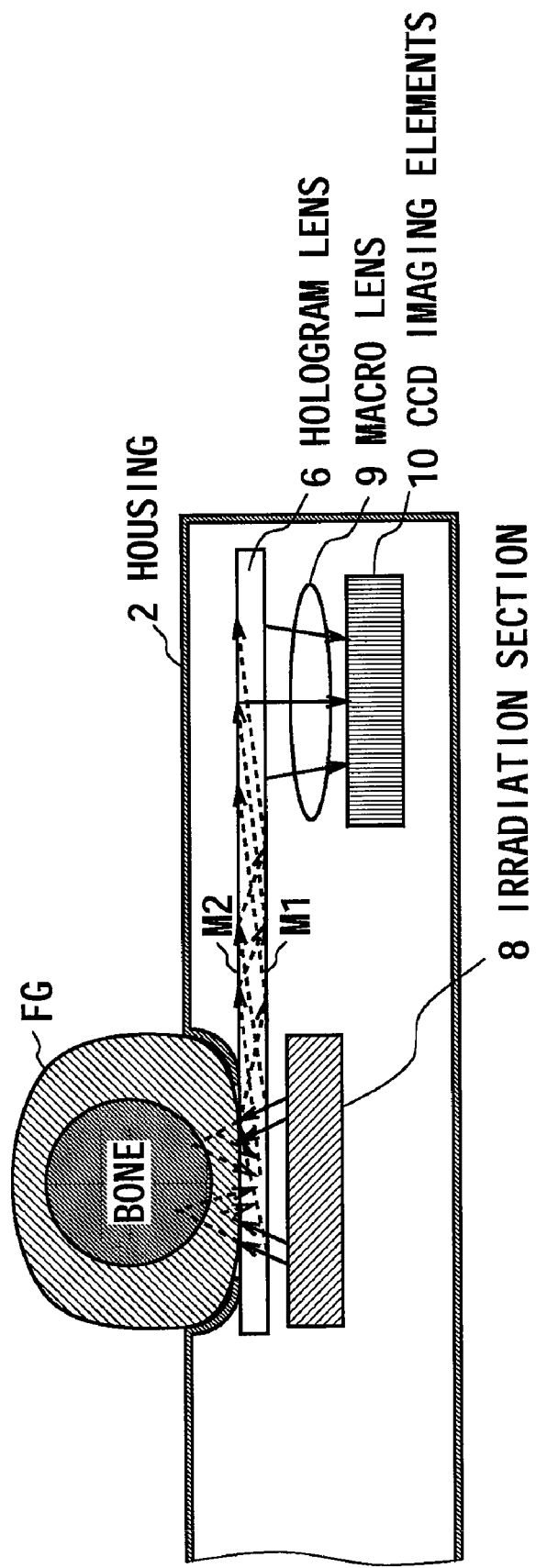
FIG. 4 is a schematic diagram illustrating the routes of NIR light.

Therefore, as shown in FIG. 4, when the NIR light sources 7 (FIG. 3) emit NIR light, the NIR light goes through the one side of hologram lens 6, and then reaches a finger FG which is placed on the surface M2 of the hologram lens 6. The NIR light then goes into the finger FG from its pad, and reaches blood vessels inside the finger FG. At this time, a part of the NIR light is absorbed in hemoglobin inside the blood vessels. And other NIR light scatters and reflects off tissues outside the blood vessels. As a result, the NIR light, which is reflecting the shape of the blood vessels, comes out from the pad of the finger FG (this NIR light is also referred to as "blood-vessel reflection light"). After that, the blood-vessel reflection light goes into the one side of hologram lens 6 from the surface M2, travels along the reflection path, and then comes out from the other side of hologram lens 6. As a result, the blood-vessel reflection light reaches the imaging plane of the CCD imaging elements 10 via the macro lens 9.

The CCD imaging elements 10 include a plurality of photoelectric transducers. The photoelectric transducers are disposed on the imaging plane in a lattice pattern. The photoelectric transducers in the CCD imaging elements 10 perform photoelectric conversion for the blood-vessel reflection light. The CCD imaging elements 10 subsequently converts the electric charge in each photoelectric transducer to blood-vessel image signals, and then outputs the blood-vessel image signals.

In this manner, the authentication device 1 can take a picture of blood vessels in a living body (i.e. the blood-vessel image signals). Based on the blood-vessel image signals, the authentication device 1 checks whether a person whose finger is now being shot has been registered or not.

In addition to the above configuration, the NIR light sources 7 are disposed in the authentication device 1 such that the NIR light from the NIR light sources 7 makes an obtuse angle with respect to a plane on which the finger FG is placed. Therefore, when the finger FG is placed on the surface M2 of the hologram lens 6, the NIR light goes into the finger FG from its side face. This reduces the amount of NIR light reflected off the surface of the finger FG, while it is difficult to reduce it when vertically emitting NIR light to the bottom face of the finger FG.

Therefore, almost only the blood-vessel reflection light reaches the imaging plane of the CCD imaging elements 10 via the hologram lens 6 and the macro lens 9. This reduces noise in the blood-vessel image signals output from the CCD imaging elements 10, because the NIR light reflected off the surface of the finger FG does not reach the CCD imaging elements 10. Therefore, based on the blood-vessel image signals, the authentication device 1 can accurately check whether the person has been registered.

As described above, the authentication device 1 utilizes blood vessels inside the finger FG to authenticate the person. When using this method of authentication, it may be more difficult to steal identities than when using fingerprints. Because fingerprints exist on the surface of the finger FG, people can steal them.

(1-2) Circuit Configuration of Authentication Device

Figure 5:
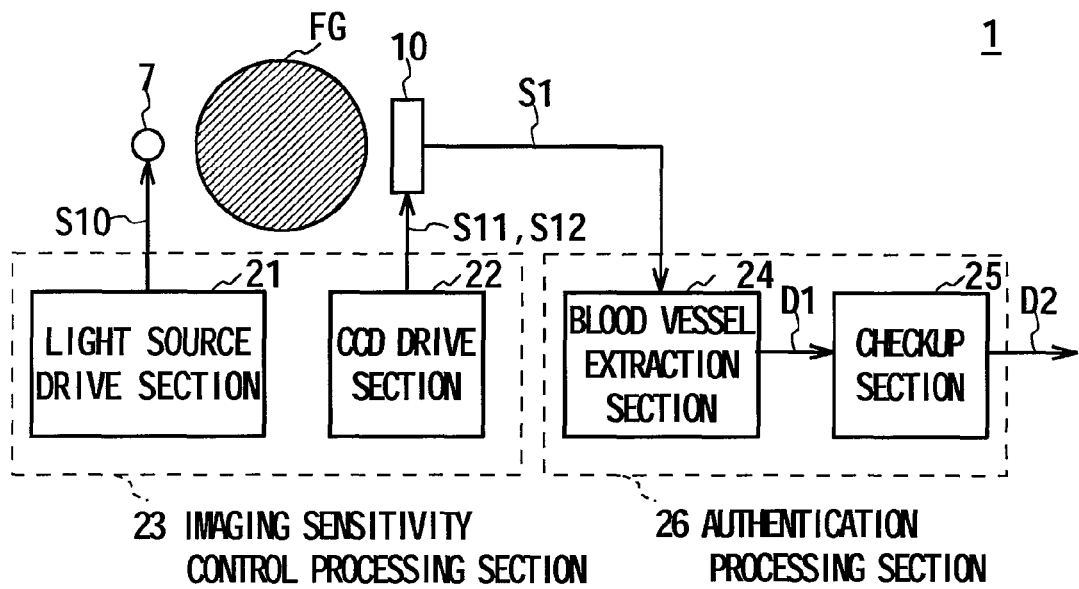
FIG. 5 is a functional block diagram showing the circuit configuration of the authentication device.

Referring to FIG. 5, the circuit configuration of the authentication device 1 will be described. The authentication device 1 includes an imaging sensitivity control processing section 23 and an authentication processing section 26. The imaging sensitivity control processing section 23 includes a light source drive section 21 and a CCD drive section 22. The authentication processing section 26 includes a blood vessel extraction section 24 and a checkup section 25. When the image-pickup start button 3A (FIG. 1) is pushed, the image-pickup start button 3A supplies a command to direct the authentication device 1 to take a picture of blood vessels. In response to the command, the authentication device 1 performs various processes.

The light source drive section 21 in the imaging sensitivity control processing section 23 boosts the voltage of its power source to a preset voltage, and then supplies this voltage to the NIR light sources 7 as light source drive signal S10 to activate the NIR light sources 7.

Therefore, in the authentication device 1, the NIR light sources 7 start to emit NIR light. This NIR light travels diagonally, and then reaches the side face of the finger FG which is placed on the surface of the hologram lens 6.

In this manner, the light source drive section 21 boosts the voltage of the power source to the preset voltage such that the NIR light has higher intensity than ordinary light in the atmosphere. This prevents the ordinary light from affecting the NIR light (the ordinary light includes visible light around the finger FG placed on the surface of the hologram lens 6).

As shown in FIG. 6A, for example, the CCD drive section 22 generates a pulse signal at a certain duty ratio, and then supplies the pulse signal to the CCD imaging elements 10 as an electric charge readout signal S11. During the unit period PT between a falling edge and next falling edge of the electric charge readout signal S11, the photoelectric transducers in the CCD imaging elements 10 store the charge. And then, the charges in the photoelectric transducers start to be read out at each falling edge.

Figure 7A:
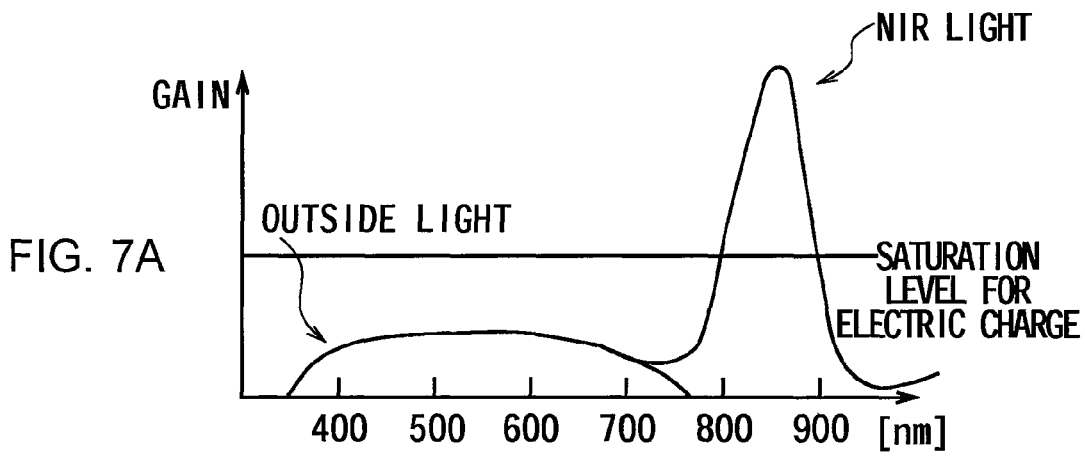
FIGS. 7A and 7B are schematic diagrams illustrating imaging sensitivity adjustment.

However, as shown in FIG. 7A, in the case in which the NIR light from the NIR light sources 7 has higher intensity than the ordinary light, the photoelectric transducers in the CCD imaging elements 10 may be saturated with the charges before the unit period PT (FIG. 6A) ends.

Accordingly, the CCD drive section 22 limits the amount of the charge stored in the photoelectric transducers (the CCD imaging elements 10) during the unit period PT (FIG. 6A).

Specifically, as shown in FIG. 6B, the CCD drive section 22 generates an electric charge reset signal S12 based on the electric charge readout signal S11. The electric charge reset signal S12 for example rises at the middle of the unit period PT to reset the photoelectric transducers (the CCD imaging elements 10) storing the charges. By the way, the time when the CCD imaging elements 10 is reset is also referred to as "reset time".

A saturation period of electric charges stored in the photoelectric transducers changes in response to the voltage of the light source drive signal supplied to the NIR light sources 7 (this voltage is equivalent to the intensity of NIR light). Therefore, based on this voltage, the reset time is set within the unit period PT.

The CCD drive section 22 supplies the electric charge reset signal S12 and the electric charge readout signal S11 to the CCD imaging elements 10. Therefore, as shown in FIG. 6C, the total amount of electric charges stored during the unit period PT is equal to the amount of electric charges stored during a period EST (the period EST is between the reset time of the electric charge reset signal S12 and the time when the electric charge readout signal S11 falls).

Figure 7B:
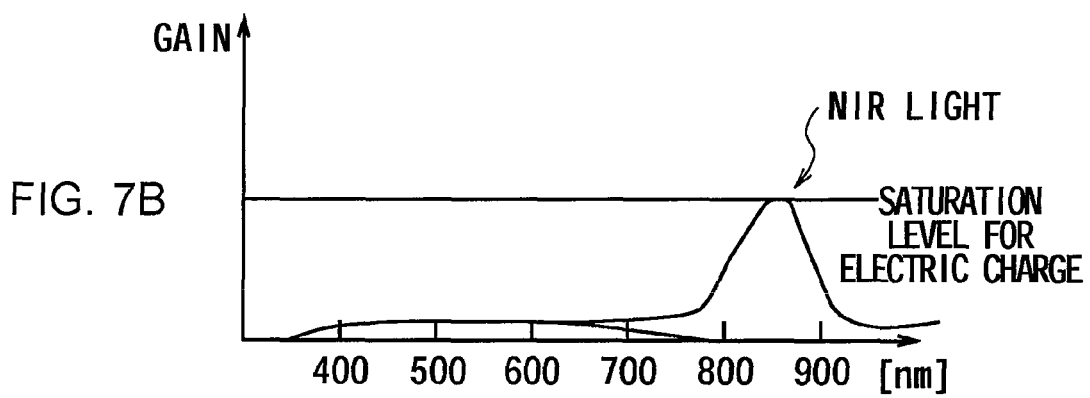

Therefore, as shown in FIG. 7B, in the CCD imaging elements 10, the amount of electric charges stored in the photoelectric transducers as a result of photoelectric conversion on the blood-vessel reflection light and ordinary light becomes relatively low. This improves the imaging sensitivity of the CCD imaging elements 10 to the blood-vessel reflection light.

In this manner, the imaging sensitivity control processing section 23 controls the NIR light sources 7 and the CCD imaging elements 10 to improve the imaging sensitivity to the NIR light.

The blood vessel extraction section 24 in the authentication processing section 26 performs analog-to-digital conversion to a blood vessel image signal S1, which is supplied from the CCD imaging elements 10, to generate blood vessel image data. The blood vessel extraction section 24 subsequently performs median filtering on the blood vessel image data to filter out noise.

The blood vessel extraction section 24 then performs for example Laplacian processing on the blood vessel image data to enhance the edges of blood vessels on the blood vessel image (the blood vessel image is equivalent to the blood vessel image signal S1). The blood vessel extraction section 24 then extracts the enhanced blood vessel images, and then generates a blood vessel image data D1 showing the enhanced blood vessel images. The blood vessel extraction section 24 subsequently supplies the blood vessel image data D1 to the checkup section 25.

By the way, the checkup section 25 has a registration database. The registration database stores the blood vessel images of legitimate users as registered blood vessel image data (the registered blood vessel image data can be obtained by the same process as that of the above-noted blood vessel extraction section 24). By calculating the cross-correlation value between the registered blood vessel image data registered in the registration database and the blood vessel image data D1 supplied from the blood vessel extraction section 24, the checkup section 25 checks the pattern of blood vessels of the blood vessel image data D1 against that of the registered blood vessel image data.

When the calculated cross-correlation value is less or equal to a prescribed threshold value, the checkup section 25 determines that the person whose finger FG is now being shot has not been registered in the registration database. When the calculated cross-correlation value is greater than the threshold value, the checkup section 25 determines that the person has been registered in the registration database, and then supplies to an external section an authentication result data D2 showing the result of this authentication.

In this manner, the authentication processing section 26 can authenticate the person based on the blood vessel image signal S1 supplied from the CCD imaging elements 10.

(1-3) Operation and Effect

The authentication device 1 with above configuration emits NIR light to the finger FG placed on the surface M2 of the hologram lens 6. And then, the authentication device 1 leads the NIR light (the blood-vessel reflection light), which comes out from the finger FG, to the imaging plane of the CCD imaging elements 10 through the reflection path formed in the hologram lens 6, as shown in FIG. 4. Specifically, the reflection path in the hologram lens 6 leads the blood-vessel reflection light, which comes from a certain position of the surface M2, to a different position of the back face M1, such that the NIR light goes into the CCD imaging elements 10.

Accordingly, in the authentication device 1, the irradiation section 8, which emits NIR light, is not overlapped with the CCD imaging elements 10. In this authentication device 1, the irradiation section 8 is substantially on the same level as the CCD imaging elements 10 under the surface M2 of the hologram lens 6. In this case, in response to the position of the CCD imaging elements 10 in the authentication device 1 (the housing 2), the reflection path in the hologram lens 6 can be decided. This provides flexibility of arrangement of the CCD imaging elements 10 in the authentication device 1 (the housing 2).

Using the hologram lens 6 with this reflection path makes the path of light simpler than using a plurality of optical lens, and also this reduces the number of components. In addition, this makes it possible to transmit enlarged images of authentication target to the imaging plane.

In this manner, the authentication device 1 with the above configuration emits NIR light to the finger FG placed on the surface M2 of the hologram lens 6. And then, the authentication device 1 leads the NIR light (the blood-vessel reflection light), which comes out from the finger FG, to the imaging plane of the CCD imaging elements 10 through the reflection path formed in the hologram lens 6. Specifically, the reflection path in the hologram lens 6 leads the blood-vessel reflection light, which comes from a certain position of the surface M2, to a different position of the back face M1, such that the NIR light goes into the CCD imaging elements 10. Therefore, in this authentication device 1, the irradiation section 8, which emit NIR light, is substantially on the same level as the CCD imaging elements 10 under the surface M2 of the hologram lens 6. Thus, the body of the authentication device 1 can be thinner.

Figure 8:
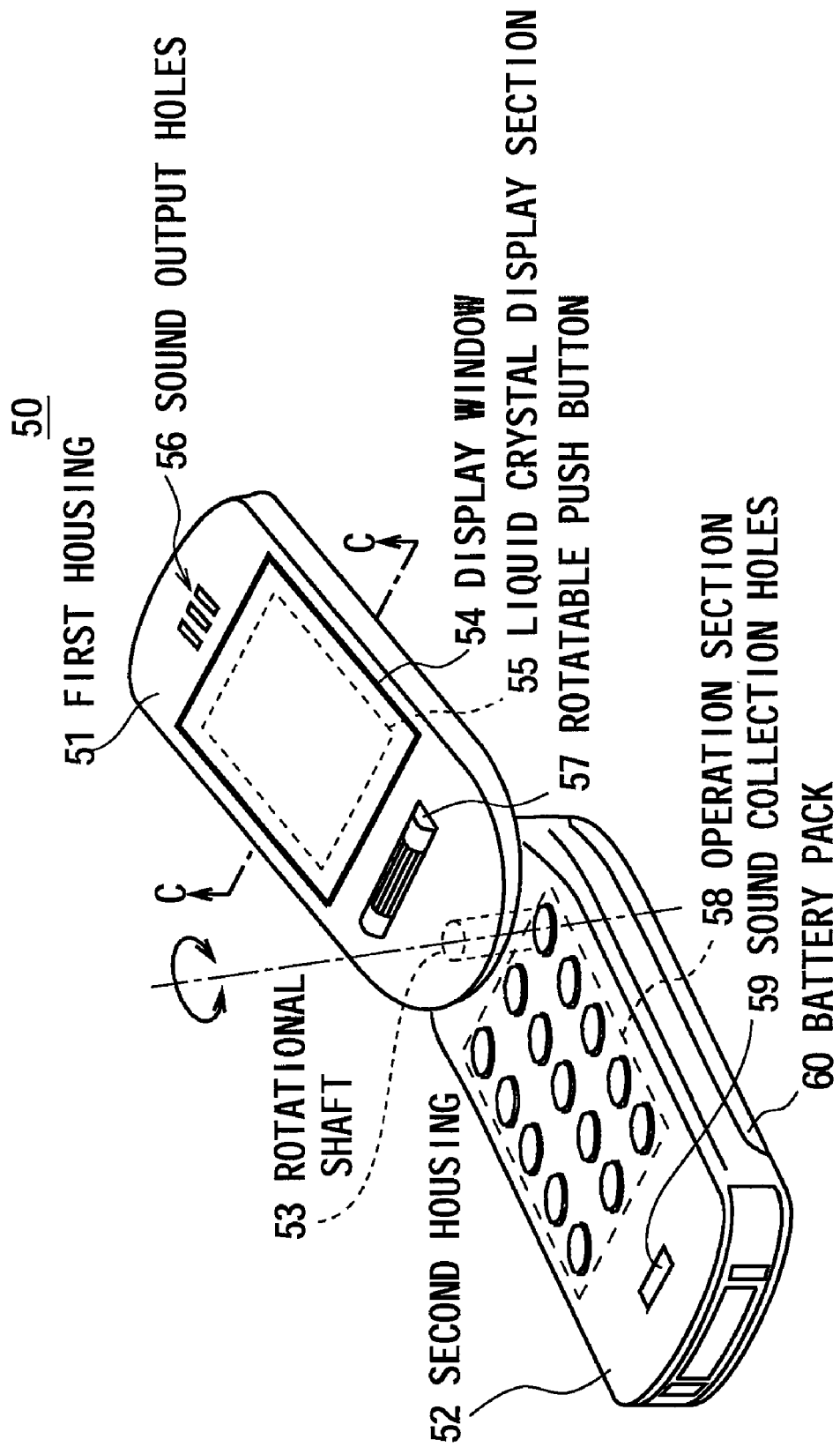
FIG. 8 is a schematic diagram showing the external structure of a portable telephone according to a second embodiment of the present invention (Opened).
Figure 9:
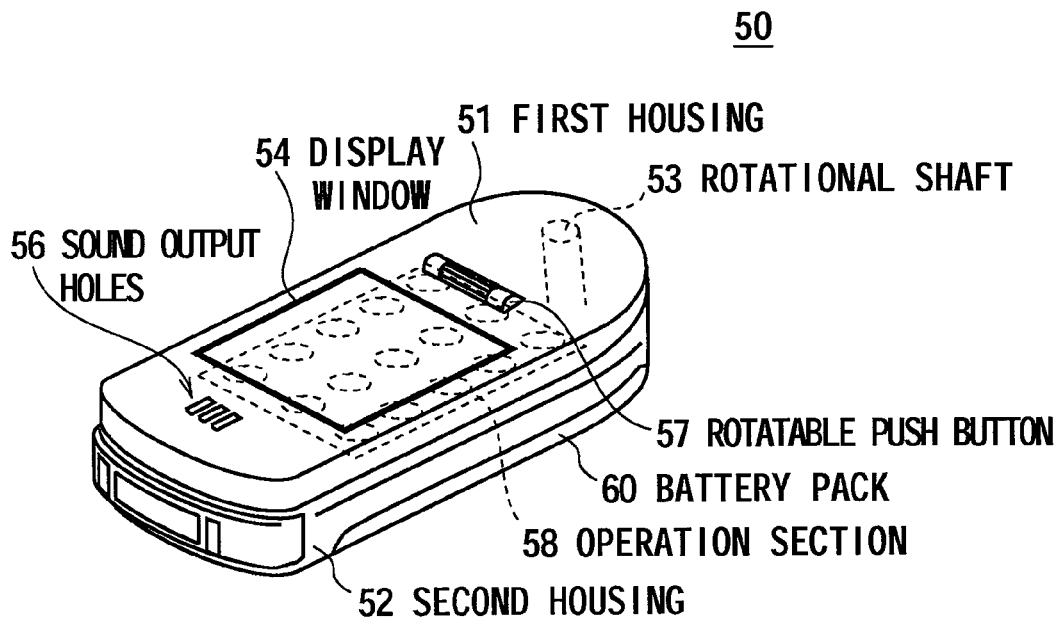
FIG. 9 is a schematic diagram showing the external structure of the portable telephone according to a second embodiment of the present invention (Closed).

(2) Second Embodiment (2-1) Overall Configuration of Portable Telephone According to Second Embodiment In FIGS. 8 and 9, the reference numeral 50 represents a portable telephone according to a second embodiment of the present invention. The portable telephone 50 includes a first housing 51, which is generally in the shape of a rectangular parallelepiped, and a second housing 52. A rotational shaft 53 is disposed around one of the shorter edges of the second housing 52. The first housing 51 is rotatably connected to the second housing 52 through the rotational shaft 53 such that the first housing 51 rotates in a substantially vertical plane.

The first housing 51 has a display window 54 on its surface. The display window 54, which is generally in the shape of a rectangle and is made of a thin glass plate, is disposed at the center of the first housing 51. A transmissive liquid crystal display section 55 is disposed under the central part of the display window 54. Sound output holes 56 are formed on the upside of the display window 54. A speaker is placed inside the first housing 51 such that the speaker outputs sound through the sound output holes 56.

A rotatable push button 57 (known as a jog dial) is placed on the downside of the display window 54. The rotatable push button 57 can be rotated and pushed by users. The liquid crystal display section 55 for example displays a cursor, and moves the cursor in response to the operation of rotating the rotatable push button 57. When the rotatable push button 57 is pushed, and then the portable telephone 50 recognizes that an item specified by the cursor is selected by users.

The second housing 52 has an operation section 58 on its surface. The operation section 58, which is disposed at the center of the second housing 52, includes a power button, a call request key, and keys for inputting characters. Pressing these operation keys for example displays a menu screen on the liquid crystal display section 55. In addition, various kinds of characters can be input by pressing these operation keys.

Sound collection holes 59 are formed on the downside of the operation section 58. A microphone is disposed inside the second housing 52 such that the microphone collects sound through the sound collection holes 59. A removable battery pack 60 can be connected to the back of the second housing 52.

As shown in FIG. 8, when the portable telephone 50 is opened (i.e. when the back face of the first housing 51 is separated from the surface of the second housing 52), a user can have the second housing 52 in one hand to make a call or to operate the rotatable push button 57 and the operation section 58. The portable telephone 50 is closed by rotating the first housing 51 onto the second housing 52, as shown in FIG. 9. Closing the portable telephone 50 protects the operation section 58 and also prevents the operation section 58 from being operated accidentally. In addition, that makes the portable telephone 50 compact enough to carry anywhere.

Figure 10:
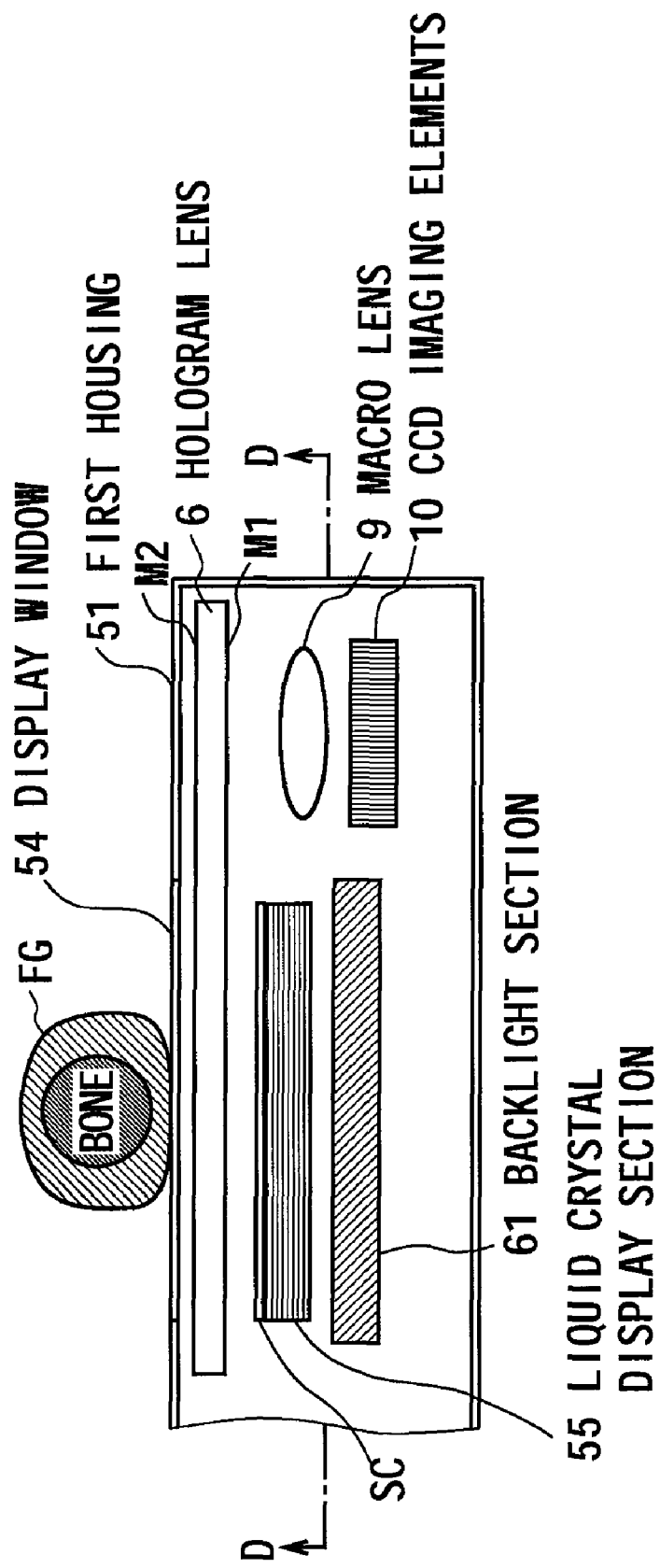
FIG. 10 is a schematic diagram showing the internal structure of a first housing.

FIG. 10 is a cross-section view of the first housing 51 taken along the line C-C' in FIG. 8. The parts of FIG. 10 have been designated by the same symbols and marks as the corresponding parts of FIG. 2. In the first housing 51, a hologram lens 6 is disposed under the display window 54. The liquid crystal display section 55 is disposed under the hologram lens 6. And then the backlight section 61 is disposed under the liquid crystal display section 55.

Figure 11:
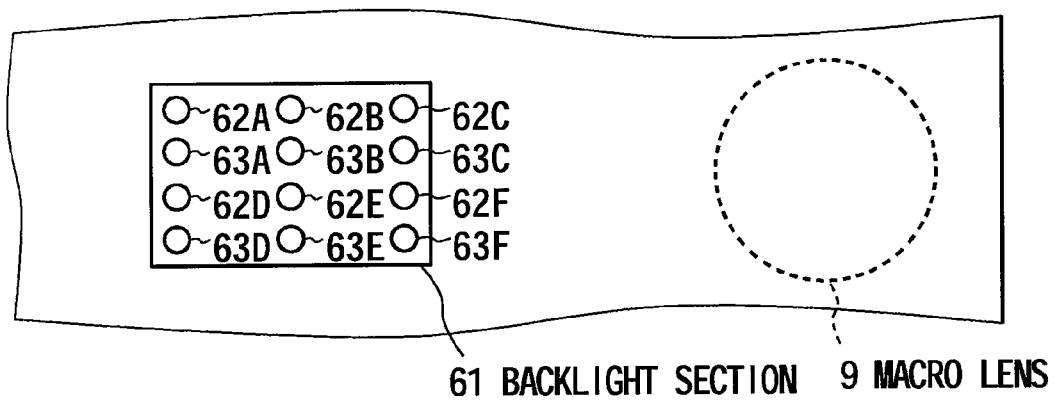
FIG. 11 is a schematic diagram showing the configuration of NIR light sources and visible light sources.

FIG. 11 is a cross-section view of the first housing 51 taken along the line D-D' in FIG. 8. Referring to FIG. 11, the surface of the backlight section 61 faces the liquid crystal display section 55. On the surface of the backlight section 61, visible light sources 62 (62A to 62F) are placed in a certain configuration to illuminate the liquid crystal display section 55 with visible light. For example, when the liquid crystal display section 55 displays screens, the visible light sources 62 illuminates the liquid crystal display section 55.

In addition, NIR light sources 63 (63A to 63F) are placed in a certain configuration on the same plane as the visible light sources 62 (62A to 62F). The NIR light sources 63 emit NIR light to take a picture of blood vessels (this NIR light is also referred to as "imaging light").

The hologram lens 6 has the same structure as the one described in the first embodiment. By the way, when displaying information on a display plane SC, the liquid crystal display section 55 emit light (this light is also referred to as "display light"). In addition, the visible light sources 62 emit visible light, and the NIR light sources 63 emit NIR light. One side portion of the hologram lens 6 leads these display light, visible light and NIR light from its back face M1 directly to its surface M2. And then, when the NIR light comes back through the display window 54, the hologram lens 6 leads this NIR light (i.e. blood-vessel reflection light) to the back face M1 of the another side portion.

Figure 12:
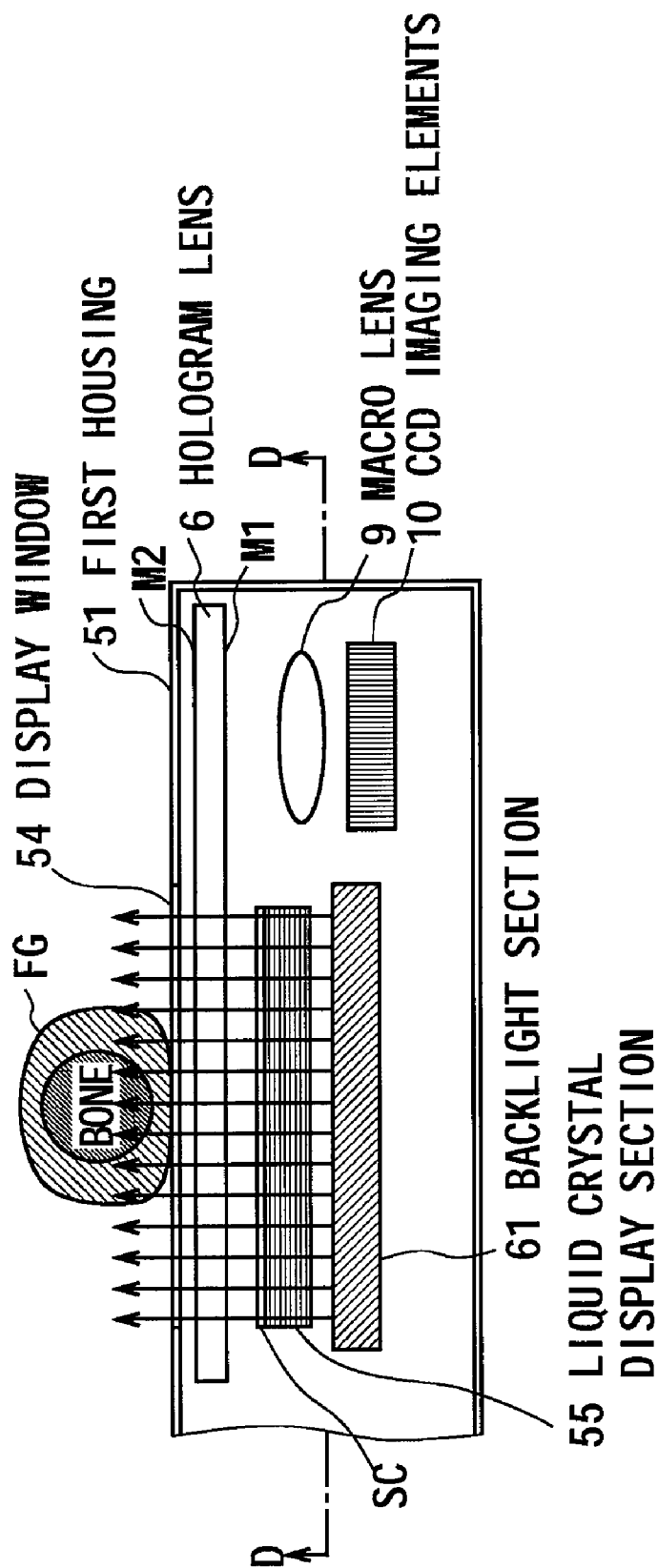
FIG. 12 is a schematic diagram illustrating NIR light emitted.

Therefore, as shown in FIG. 12, when the finger FG is put on the surface of the display window 54, NIR light from the NIR light sources 63 (FIG. 11) reaches blood vessels inside the finger FG via the liquid crystal display section 55 and the hologram lens 6. Then, this NIR light comes out from the finger FG, and goes into the one side portion of the hologram lens 6 through its surface M2 as blood-vessel reflection light. After that, this blood-vessel reflection light travels in the same way as the one illustrated by FIG. 4. Therefore the blood-vessel reflection light comes out from the another side portion of the hologram lens 6, and reaches the imaging plane of the CCD imaging elements 10 via the macro lens 9.

In this manner, the display plane SC of the liquid crystal display section 55 of the portable telephone 50 works as if an imaging plane of camera to take a picture of blood vessels inside the finger FG placed on the display window 54 which is located above the display plane SC.

(2-2) Circuit Configuration of Portable Telephone

Figure 13:
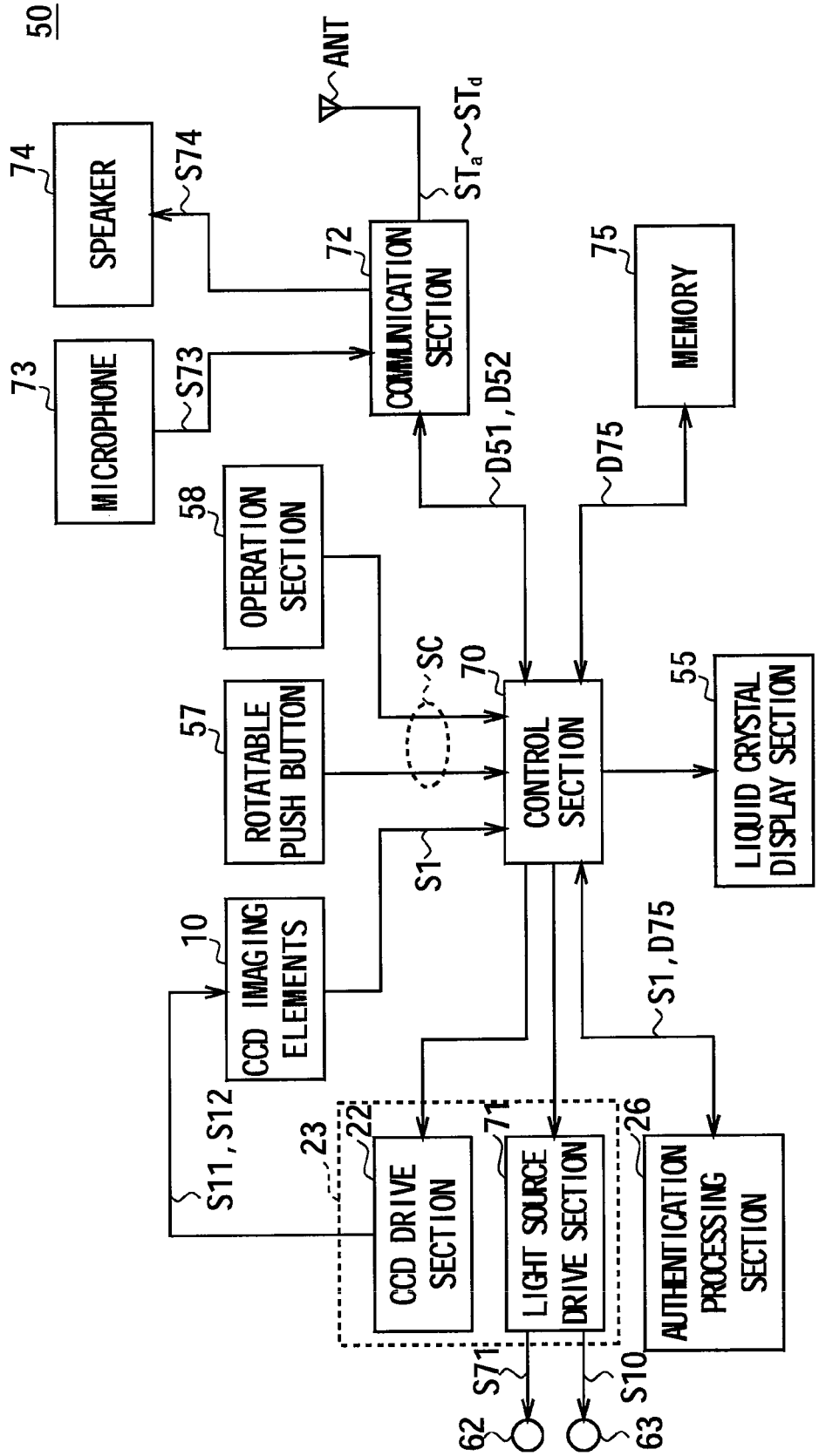
FIG. 13 is a functional block diagram showing the circuit configuration of the portable telephone.

FIG. 13 shows the circuit configuration of the portable telephone 50 (the parts of FIG. 13 have been designated by the same symbols and marks as the corresponding parts of FIG. 5). The portable telephone 50 has a control section 70 with a microcomputer configuration. The control section 70 includes a Central Processing Unit (CPU), which takes overall control of the portable telephone 50; a Read Only Memory (ROM), which stores various kinds of programs; a Random Access Memory (RAM), which the CPU uses to perform processes; and a clock generator.

When a user operates the rotatable push button 57 or the operation section 58, the rotatable push button 57 or the operation section 58 supplies an operation input signal SC to the control section 70.

Based on the operation input signal SC, the control section 70 recognizes user's instructions. In response to the instructions, the control section 70 then performs various processes based on various kinds of control programs stored in the ROM, and displays resulting data on the display plane SC of the liquid crystal display section 55.

When displaying the data on the display plane SC, the control section 70 controls a light source drive section 71 to supply a power supply voltage, which is charged in the battery pack 60, to the visible light sources 62 as a light source drive signal S71. As a result, the visible light sources 62 starts to emit visible light to the liquid crystal display section 55 to illuminate the liquid crystal display section 55.

When the control section 70 recognizes, based on the operation input signal SC, that a user starts to call someone's cell phone, the control section 70 goes into speech mode to control a communication section 72.

Accordingly, the communication section 72 performs modulation and amplification process to sound signals S73 supplied from a microphone 73 to generate transmission signals STa (this microphone 73 collects sound through the sound collection holes 59 (FIG. 8), and transforms it to the sound signals S73). The communication section 72 then transmits the transmission signals STa to a base station (not shown) via an antenna ANT. As a result, the transmission signals STa are received by the intended cell phone.

In addition, the communication section 72 receives transmission signals STb, which are transmitted from other cell phones via a base station (not shown), through the antenna ANT, and then performs amplification and demodulation process to the transmission signals STb. The communication section 72 subsequently supplies the resulting sound signals S74 to a speaker 74. Based on the sound signals S74, the speaker 74 then outputs sound via the sound output holes 56 (FIG. 8).

When a user specifies a communication target and data to be transmitted to this target, and then operates the portable telephone 50 to start communication, the control section 70 recognizes these user's instructions based on the operation input signal SC and goes into communication mode to control the communication section 72 (The data to be transmitted is also referred to as "transmission-target data"). The control section 70 then supplies the transmission-target data D51 to the communication section 72. The transmission-target data D51 include data generated on the RAM and personal data stored in a memory 75.

The communication section 72 performs digital-to-analog conversion, modulation and amplification process to the transmission-target data D51, and then transmits the resulting transmission signals STc to a base station (not shown) via an antenna ANT. As a result, the transmission signals STc are received by the intended target.

In addition, the communication section 72 receives transmission signals STd, which are transmitted from the communication target via a base station (not shown), through the antenna ANT, and then performs amplification, demodulation and analog-to-digital conversion process to the transmission signals STd. The communication section 72 subsequently supplies the resulting data (referred to as "communication-target-transmission data") D52 to the control section 70.

In response to the contents of the communication-target-transmission data D52, the control section 70 performs various processes, such as supplying to the communication section 72 new transmission-target data D51 to respond to the communication-target-transmission data D52.

(2-3) Blood Vessel Authentication Process

In addition to the above configuration, the portable telephone 50 authenticates a user who uses this portable telephone 50 with his/her blood vessels before going into the above-noted communication mode (Therefore, the blood vessels are an authentication target).

In this case, when a user specifies a communication target and data to be transmitted to this target, and then operates the portable telephone 50 to start communication, the control section 70 goes into blood vessel imaging mode before getting into the communication mode. In the blood vessel imaging mode, the control section 70 displays a notification screen on the display plane SC of the liquid crystal display section 55 to ask a user to put his/her finger FG on the liquid crystal display section 55. When a certain period of time has passed since when the control section 70 started displaying the notification screen, the control section 70 displays a white screen on the display plane SC and starts to control the imaging sensitivity control processing section 23.

At this time, the imaging sensitivity control processing section 23 performs process in the same way as the above-noted first embodiment. That is to say, to improve the imaging sensitivity to NIR light, the imaging sensitivity control processing section 23 supplies the light source drive signal S10 to the NIR light sources 63, and also supplies the electric charge readout signal S11 and the electric charge reset signal S12 to the CCD imaging elements 10. In this manner, the NIR light sources 63 and the CCD imaging elements 10 starts operating.

After that, when receiving the blood vessel image signal S1 from the CCD imaging elements 10, the control section 70 supplies this blood vessel image signal S1 and a registered blood vessel image data D75 to the authentication processing section 26 (The registered blood vessel image data D75, which has been registered in the memory 75, represents an image of legitimate user's blood vessels). The control section 70 subsequently starts to control the authentication processing section 26.

Accordingly, the authentication processing section 26 performs process in the same way as the above-noted first embodiment. That is to say, the authentication processing section 26 performs analog-to-digital conversion, Laplacian and median filtering process to the blood vessel image signal S1 to generate the blood vessel image data D1 (FIG. 5). Based on the blood vessel image data D1 and the registered blood vessel image data D75 supplied from the memory 75, the authentication processing section 26 subsequently checks whether a person whose finger FG is now being shot is legitimate or not, and then notifies the control section 70 of the result of the check.

When the control section 70 is notified of the result of the check, the control section 70 displays this result on the display plane SC of the liquid crystal display section 55. In addition, when this result tells that the person is legitimate, the control section 70 then moves into the communication mode from the blood vessel imaging mode.

In this manner, in order for only the legitimate user to be able to communicate with the communication target, the portable telephone 50 checks whether a user who is currently using this portable telephone 50 is legitimate or not before starting communication.

(2-4) Display Control Process

By the way, in the above-noted first embodiment, the direction of the NIR light emitted from the NIR light sources 7 has been previously set such that this NIR light makes an obtuse angle with respect to a plane on which the finger FG is placed. By contrast, in the portable telephone 50, the direction of the NIR light emitted from the NIR light sources 63 (FIG. 11) in the backlight section 61 (FIG. 11) is not specified.

Accordingly, as shown in FIG. 12, some of the NIR light from the NIR light sources 63 may travel vertically with respect to a bottom face of the finger FG on the display window 54. This increases the amount of the NIR light reflected off the surface of the finger FG, and then increases noise in the blood vessel image signal S1 (FIG. 13) output from the CCD imaging elements 10.

Figure 14:
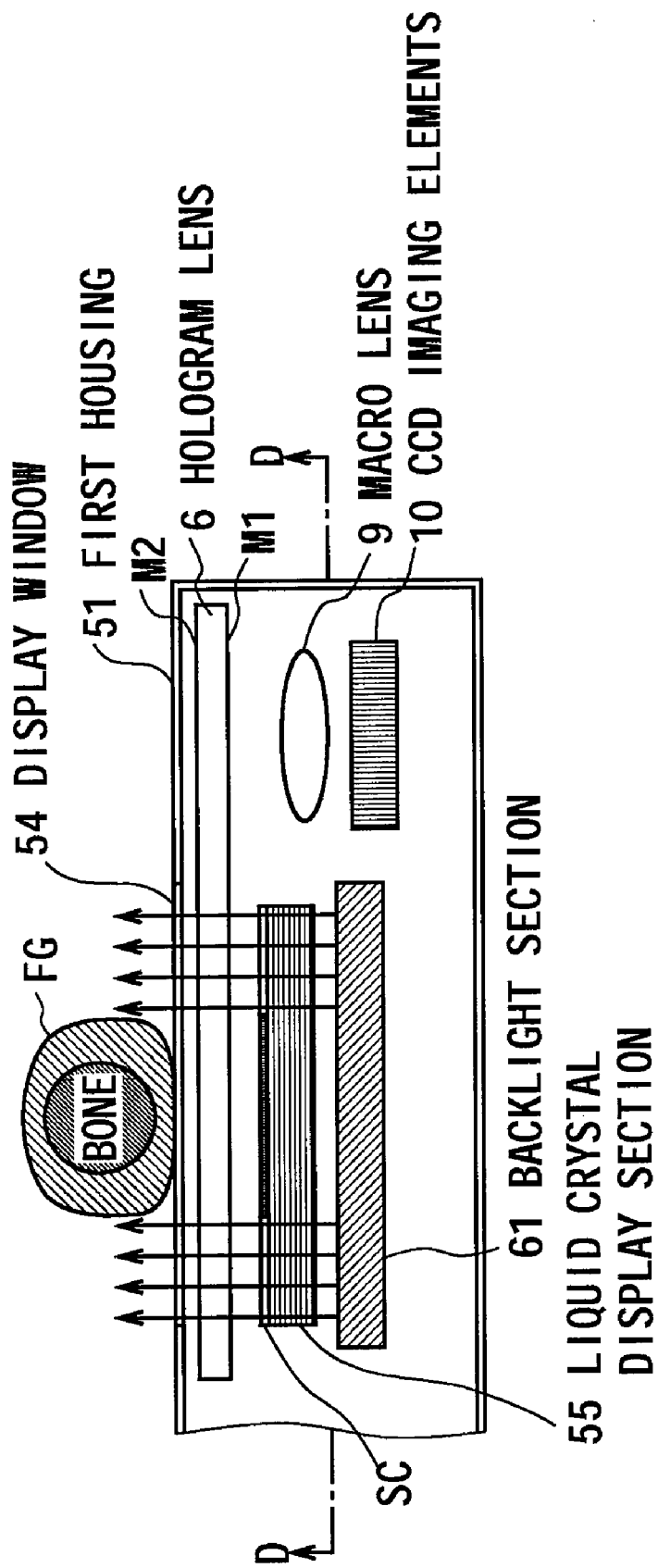
FIG. 14 is a schematic diagram illustrating NIR light shut out.

To solve this problem, the portable telephone 50 controls the liquid crystal display section 55 to shut out a part of NIR light, which is emitted from the NIR light sources 63 directly beneath the finger FG on the display window 54, as shown in FIG. 14.

To do that, the control section 70 in the blood vessel imaging mode controls the imaging sensitivity control processing section 23 to adjust the NIR light sources 63 and the CCD imaging elements 10 to improve the imaging sensitivity to NIR light, and detects an outline of the finger in the blood vessel image, which is obtained from the blood vessel image signal S1 output from the CCD imaging elements 10.

Figure 15:
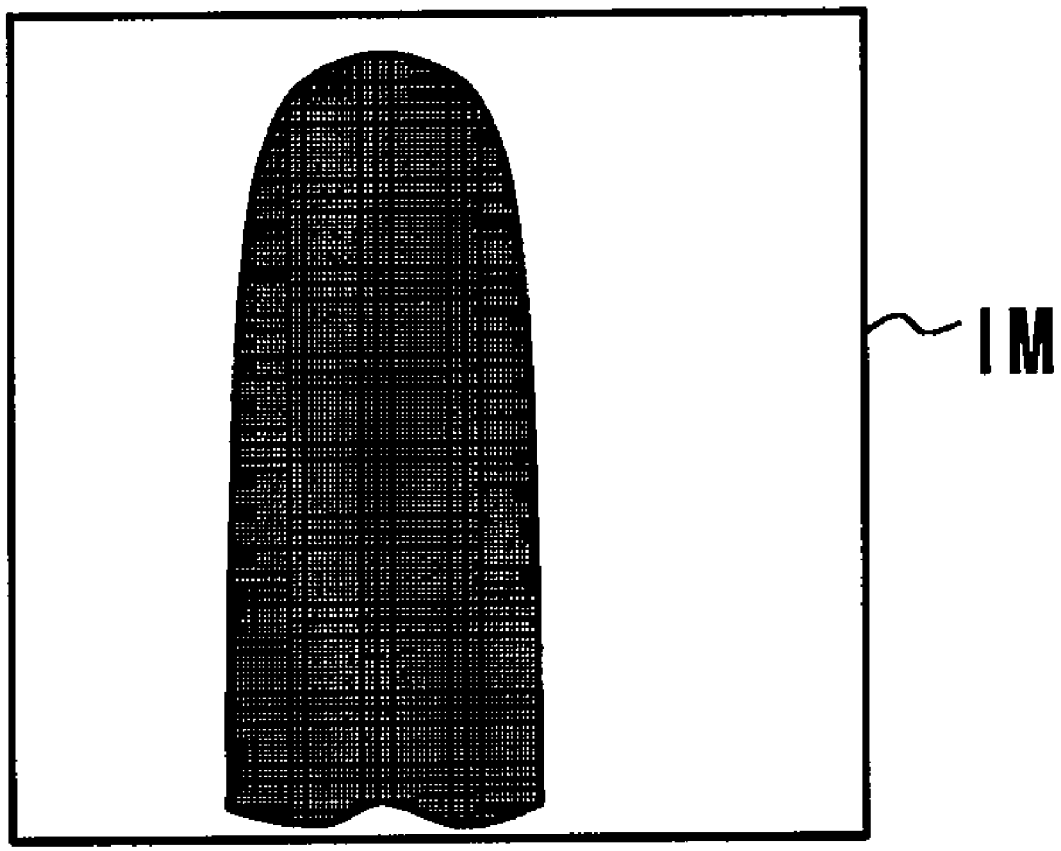
FIG. 15 is a schematic diagram showing an example of a finger-shield screen.

The control section 70 then processes all pixels inside the outline of the finger to lower the luminance level of these pixels as much as possible, as shown in FIG. 15. In addition, the control section 70 raises the luminance level of other pixels outside the outline as much as possible. In this manner, the control section 70 generates data of a shield screen IM that includes an image in the shape of the finger FG, which a user currently puts above the display plane SC (This shield screen is also referred to as "finger-shield screen"). The control section 70 then displays the finger-shield screen IM on the display plane SC of the liquid crystal display section 55 based on the finger-shield screen data.

As a result, as shown in FIG. 14, in the first housing 51 of the portable telephone 50, the liquid crystal display section 55 shuts out the NIR light that travels vertically with respect to the finger FG on the display window 54 (i.e. the liquid crystal display section 55 shuts out the NIR light emitted from the NIR light sources 63 directly beneath the finger FG). Therefore, the side faces of the finger FG is illuminated by the NIR light that travels diagonally with respect to the finger FG (i.e. the finger FG is illuminated by the NIR light that makes an obtuse angle with a plane on which the finger FG is placed). After that, in the same way as the one described by FIG. 4, after coming out from the finger FG, the NIR light (the blood-vessel reflection light) goes through the hologram lens 6 and macro lens 9, and then reaches the imaging plane of the CCD imaging elements 10.

That decreases the amount of the NIR light reflected off the surface of the finger, and then reduces noise in the blood vessel image signal S1 in the same way as the above-noted first embodiment. This blood vessel image signal S1 is supplied from the CCD imaging elements 10 to the control section 70.

Based on this blood vessel image signal S1, the control section 70 controls the authentication processing section 26 to check whether the person has been registered or not, and then displays the result of the check on the display plane SC of the liquid crystal display section 55. When the result of the check tells that the person has been registered, the control section 70 moves into the communication mode from the blood vessel imaging mode.

In this manner, the control section 70 can shut out the NIR light emitted from the NIR light sources 63 directly beneath the finger FG on the display window 54.

(2-5) Operation and Effect

In the portable telephone 50 with the above configuration, the backlight section 61, which is disposed behind the liquid crystal display section 55, emits illumination light and NIR light. After that, the NIR light goes into the finger FG above the liquid crystal display section 55, and then comes out from the finger FG as blood-vessel reflection light. And then, the reflection path in the hologram lens 6 leads only the blood-vessel reflection light from the surface M2 of the one side portion of the hologram lens 6 to the back face M1 of another side portion. As a result, the blood-vessel reflection light reaches the imaging plane of the CCD imaging elements 10.

Therefore, the portable telephone 50 obtains the same benefits as the above-noted first embodiment. In addition, since this portable telephone 50 utilizes the display plane SC of the liquid crystal display section 55 as if it were an imaging plane to take a picture of blood vessels inside the finger FG, there is no need to provide a specific space on the first housing 51 for the finger FG to be placed. In addition, there is no need to form an image pickup aperture through which the blood-vessel reflection light from the finger FG travels. In this manner, even if the portable telephone 50 does not have the specific space and the image pickup aperture, the portable telephone 50 can emit NIR light to the finger FG and therefore take a picture of blood vessels inside the finger FG.

In addition, based on images generated by the CCD imaging elements 10, the portable telephone 50 controls the liquid crystal display section 55 to shut out a part of NIR light, which is emitted from the backlight section 61 via the crystal display section 55. That is to say, the portable telephone 50 controls the liquid crystal display section 55 to shut out the NIR light that travels vertically with respect to the authentication target (i.e. the finger FG), as shown in FIG. 14.

By using this method, there is no need to previously set the direction of NIR light to reduce the amount of the NIR light reflected off the surface of the finger. Nonetheless, this method can reduce noise in the blood vessel image signal S1 and noise in the images generated by the CCD imaging elements 10. In addition, this method can prevent the interference between the NIR light, which travels through the liquid crystal display section 55, and the blood-vessel reflection light, which comes out from the finger FG. That improves the precision of authentication.

Specifically, the portable telephone 50 controls the liquid crystal display section 55 such that the liquid crystal display section 55 displays an image in the shape of the finger FG (the finger FG has blood vessels to be authenticated inside), and this image shuts up the NIR light. This image helps a user put his/her finger FG precisely, because he/she can visually check if his/her finger FG is placed on the exact position.

In this manner, in the portable telephone 50 with the above configuration, the backlight section 61, which is disposed behind the liquid crystal display section 55, emits illumination light and NIR light. After that, the NIR light goes into the finger FG above the liquid crystal display section 55, and then comes out from the finger FG as blood-vessel reflection light. And then, the reflection path in the hologram lens 6 leads only the blood-vessel reflection light from the surface M2 of the one side portion of the hologram lens 6 to the back face M1 of another side portion. As a result, the blood-vessel reflection light reaches the imaging plane of the CCD imaging elements 10. This method makes the body of the portable telephone 50 thinner like the above-noted first embodiment. In addition, since this portable telephone 50 utilizes the display plane SC of the liquid crystal display section 55 as if it were an imaging plane to take a picture of blood vessels inside the finger FG, there is no need to provide a specific space on the first housing 51 for the finger FG to be placed. In addition, there is no need to form an image pickup aperture through which the blood-vessel reflection light from the finger FG travels. In this manner, even if the portable telephone 50 does not have the specific space and the image pickup aperture, the portable telephone 50 can emit NIR light to the finger FG and therefore take a picture of blood vessels inside the finger FG. Thus, the portable telephone 50 can be miniaturized.

(3) Other Embodiments

In the above-noted embodiments, an emitter means emits the NIR light as an imaging light (This NIR light has wavelength dependence on blood vessels inside a living body).

However, the present invention is not limited to this. The emitter means may emit different kinds of light. For example, a marker specific to a certain unique structure (other than the blood vessels) inside a living body is injected into a living body. And then the emitter means may emit to the living body a certain light that has wavelength dependence on the marker.

In the above-noted embodiments, the device (the authentication device 1 or the portable telephone 50) utilizes each person's unique structure inside a living body to authenticate. However, the present invention is not limited to this. The device can also utilize each person's unique structure on the surface of living body, such as fingerprints. In this case, it is desirable to use the method of the second embodiment, because the device can utilize the illumination light (visible light) from the liquid crystal display section 55 as imaging light. This reduces the number and types of the light sources in the backlight section 61 which miniaturizes the device.

In the above-noted embodiments, a finger is a target of illumination. However, the present invention is not limited to this. Different parts of a living body (such as a palm of a hand and an arm) can be illuminated instead of a finger. Using different parts of a living body can even obtain the same benefits as the above-noted embodiments.

In addition, the imaging light can illuminate not only a target of authentication (such as blood vessels) but also a target to be copied (such as a surface of a printed material). Even in this case, the same effect as the above-noted embodiments can be obtained.

In the above-noted embodiments, the hologram lens 6, which is in the shape of a flat plate, is applied as light transmission means (The light transmission means leads an imaging light that comes from one face directly to another face, and leads an imaging light that comes from a certain position of the another face to a different position of the one face). However, the present invention is not limited to this. Differently-shaped hologram lens 6 (such as curved or U-shaped hologram lens 6) can be applied as the light transmission means. Even in this case, the same effect as the above-noted embodiments can be obtained.

In the above-noted embodiments, the reflection path in the hologram lens 6 is formed such that the reflection path leads light that comes from the surface M2 of the one side portion of the hologram lens 6 to the back face M1 of another side portion. However, the present invention is not limited to this. For example, depending on the available space for placing components inside the housing 2 (or the first housing 51), the shape of hologram lens 6, and the like, the reflection path can be changed. For example, the reflection path in the hologram lens 6 can be formed such that the reflection path leads light that comes from the surface M2 of the central portion of the hologram lens 6 to the back face M1 of the another side portion.

In the above-noted embodiment, the incident characteristic of the hologram lens 6 selectively allows the NIR light (which has wavelength dependence on the blood vessels inside a living body) to penetrate the hologram lens 6. However, the present invention is not limited to this. The hologram lens 6 may allow a light with different wavelength to penetrate it, for example, when a structure on the surface of living body (such as fingerprints) is authenticated.

In addition, the incident characteristic of the hologram lens 6 may allow only the NIR light of wavelength 900 to 1000 nm to penetrate the hologram lens 6. This NIR light has wavelength dependence on both oxy-hemoglobin and deoxy-hemoglobin in blood vessels (This wavelength dependence is also referred to as "oxy- and deoxy-hemoglobin dependence wavelength range"). This makes it possible to obtain the blood-vessel reflection light that precisely reflects the shape of the blood vessels inside the tip of the finger, since this part of the finger includes both oxy-hemoglobin and deoxy-hemoglobin (This blood-vessel reflection light goes through the hologram lens 6 and then reaches the imaging plane of the CCD imaging elements 10). That allows the device to precisely authenticate based on the blood vessels.

In the above-noted embodiments, the CCD imaging elements 10 are applied as image pickup means (The image pickup means picks up an image equivalent to an imaging light). However, the present invention is not limited to this. Other components (such as Complementary Metal Oxide Semiconductor (CMOS)) can be applied as the image pickup means.

In the above-noted embodiments, the transmissive liquid crystal display section 55 is applied as display means (The display means displays a display content on a display plane). However, the present invention is not limited to this. For example, a liquid crystal display section, at least a part of which is transmissive, can be applied as the display means. Even in this case, the same effect as the above-noted embodiments can be obtained.

In the above-noted embodiments, based on the image picked up by the image pickup means, a control means controls the display means such that the display means shuts out the imaging light that travels in a vertical direction with respect to a target of authentication, the imaging light being emitted through the display means. Specifically, the control means displays on the display plane SC the finger-shield screen IM which is in the shape of a part of living body (i.e. the finger FG) including a target of authentication (i.e. the blood vessels). However, the present invention is not limited to this. The control means may display on the display plane SC a differently-shaped shield screen which can cover the part of living body (the finger FG).

In the above-noted first embodiment, the authentication device 1 (FIGS. 1 and 2) is applied as an image pickup apparatus. In the above-noted second embodiment, the portable telephone 50 (FIGS. 8 to 10) is applied as the image pickup apparatus. However, the present invention is not limited to this. For example, the image pickup apparatus may include other kinds of household and commercial electric appliance, such as Personal Digital Assistant (PDA), photocopier, scanner, personal computer, router and television apparatus. When one of these devices is selected as the image pickup apparatus, the irradiation section 8, hologram lens 6, macro lens 9 and CCD imaging elements 10 shown in FIG. 2 may be incorporated into the selected device in the same configuration as the one described in FIG. 2. In this case, the same effect as the above-noted embodiments can be obtained.

The device according to an embodiment of the present invention, for example, can be utilized when taking a picture of a target to authenticate or when copying a target.

It should be understood by those skilled in the art that various modifications, combinations, sub-combinations and alterations may occur depending on design requirements and other factors insofar as they are within the scope of the appended claims or the equivalents thereof.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An authentication apparatus comprising:
   an emitter section for emitting an imaging light;
   a position detecting section for detecting a position of a target of authentication;
   a display section positioned in which said imaging light permeates;
   a control section for controlling whether to emit the imaging light to said target of authentication, based on the position of said detected position of said target of authentication; and
   an authentication section for authenticating based on data obtained from said imaging light.

2. The authentication apparatus of claim 1, which includes a lens transmission section disposed between said display section and said emitter section, said lens transmission section having a first face and a second face.

3. The authentication apparatus of claim 2, wherein when said imaging light is emitted, said lens transmission section leads said emitted imaging light, said emitted imaging light coming from said first face directly to said second face.

4. The authentication apparatus of claim 2, wherein when said imaging light is emitted, said lens transmission section leads said emitted imaging light, said emitted imaging light coming from a first position of said second face to a second position of said first face.

5. The authentication apparatus of claim 1, wherein when said imaging light is emitted, said control section shuts out imaging light traveling in a vertical direction with respect to said target of authentication.

6. The authentication apparatus of claim 1, wherein said target of authentication is inside a living body, said living body having a shape.

7. The authentication apparatus of claim 6, wherein when said imaging light is emitted, said control section shuts out imaging light corresponding to the shape of said living body.

8. An authentication apparatus comprising:
   a display plane;
   an emitter;
   a processor; and
   a memory device which stores instructions, which when executed by the processor, cause the processor to operate with the display plane and the emitter to:
   (a) detect a position of a target of authentication;
   (b) determine whether to emit an imaging light to said target of authentication based on said detected position of said target of authentication, wherein when said imaging light is emitted, said imaging light permeates said display plane;
   (c) authenticate based on data obtained from said imaging light.

9. The authentication apparatus of claim 8, which includes a lens transmission section disposed between said display plane and said emitter, said lens transmission section having a first face and a second face.

10. The authentication apparatus of claim 9, wherein when executed by the instructions, the instructions cause the processor to operate with the display plane, emitter, and the lens transmission section to, when said imaging light is emitted, lead said emitted imaging light, said emitted imaging light coming from said first face directly to said second face.

11. The authentication apparatus of claim 9, wherein when executed by the instructions, the instructions cause the processor to operate with the display plane, emitter, and the lens transmission section to, when said imaging light is emitted, lead said emitted imaging light, said emitted imaging light coming from a first position of said second face to a second position of said first face.

12. The authentication apparatus of claim 8, wherein when executed by the instructions, the instructions cause the processor to shut out imaging light traveling in a vertical direction with respect to said target of authentication.

13. The authentication apparatus of claim 8, wherein said target of authentication is inside a living body, said living body having a shape.

14. The authentication apparatus of claim 13, wherein when executed by the instructions, the instructions cause the processor to shut out imaging light corresponding to the shape of said living body.

15. A method of operating an authentication apparatus having instructions, said method comprising:
   (a) causing a processor to execute the instructions to detect a position of a target of authentication;
   (b) causing the processor to execute the instructions to determine whether to emit an imaging light to said target of authentication based on said detected position of said target of authentication,
   (c) if the determination is to emit the imaging light, causing an emitter to emit said imaging light, wherein when said imaging light is emitted, said imaging light permeates a display plane;
   (c) causing the processor to execute the instructions to authenticate based on data obtained from said imaging light.

16. The authentication apparatus of claim 15, which includes, when said imaging light is emitted, causing a lens transmission section to lead said emitted imaging light, said lens transmission section having a first face and a second face, said emitted imaging light coming from said first face directly to said second face.

17. The authentication apparatus of claim 16, which includes, when said imaging light is emitted, causing the lens transmission section to lead said emitted imaging light, said emitted imaging light coming from a first position of said second face to a second position of said first face.

18. The authentication apparatus of claim 15, which includes causing the processor to execute the instructions to shut out imaging light traveling in a vertical direction with respect to said target of authentication.

19. The authentication apparatus of claim 15, wherein said target of authentication is inside a living body, said living body having a shape.

20. The authentication apparatus of claim 19, which includes causing the processor to execute the instructions to shut out imaging light corresponding to the shape of said living body.

* * * * *